United States Patent
Weida et al.

(10) Patent No.: US 8,068,521 B2
(45) Date of Patent: *Nov. 29, 2011

(54) LASER SOURCE THAT GENERATES A PLURALITY OF ALTERNATIVE WAVELENGTH OUTPUT BEAMS

(75) Inventors: Miles James Weida, Poway, CA (US); Russ Pritchett, Montara, CA (US); David F. Amone, Mountain View, CA (US)

(73) Assignee: Daylight Solutions, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/960,742

(22) Filed: Dec. 6, 2010

(65) Prior Publication Data
US 2011/0096800 A1    Apr. 28, 2011

Related U.S. Application Data

(63) Continuation of application No. 12/353,223, filed on Jan. 13, 2009, now Pat. No. 7,848,382.

(60) Provisional application No. 61/021,854, filed on Jan. 17, 2008.

(51) Int. Cl.
*H01S 3/10* (2006.01)
*H01S 3/08* (2006.01)

(52) U.S. Cl. ............... 372/20; 372/92; 372/102

(58) Field of Classification Search .............. 372/20, 372/92, 98–99, 102
See application file for complete search history.

(56) References Cited

U.S. PATENT DOCUMENTS
2,684,015 A    7/1954   Grey
(Continued)

FOREIGN PATENT DOCUMENTS
DE         10205310 A1    9/2003
(Continued)

OTHER PUBLICATIONS

Hildebrandt, L. et al.,"Quantum cascade external cavity laser systems in the mid-infrared spectral range," 2004 Sacher Lasertechnik Group, Marburg, Germany (provided in U.S. Appl. No. 12/353,223).

(Continued)

*Primary Examiner* — Jessica Stultz
*Assistant Examiner* — Phillip Nguyen
(74) *Attorney, Agent, or Firm* — Roeder & Broder LLP (57) ABSTRACT

A laser source (10) for emitting a set of sequential, different wavelength output beams (12) includes a gain medium (16), a feedback assembly (26) and a control system (30). The gain medium (16) includes a first facet (16A), and the gain medium (16) generates a beam (12A) that exits the first facet (16A). The feedback assembly (26) includes a feedback device (40) and a device mover (42). The feedback device (40) is positioned in the path of the beam (12A) that exits the first facet (16A) and the feedback device (40) redirects at least a portion of the beam (12A) back to the gain medium (16). The device mover (42) continuously adjusts an angle of incidence ($\theta$) of the beam (12A) on the feedback device (40). The control system (30) selectively directs pulses of power to the gain medium (16) as the device mover (42) is continuously adjusting the angle of incidence ($\theta$) of the beam (12A). Further, the laser source (10) can include a position detector (28) that generates a position signal that relates to the angle of incidence ($\theta$) of the beam (12A) on the feedback device (40). In this embodiment, the control system (30) can selectively direct pulses of power to the gain medium (16) based on the position signal from the position detector (28). Further, the control system (30) can determine a center wavelength of the output beam (12) based on the position signal.

22 Claims, 4 Drawing Sheets

U.S. PATENT DOCUMENTS

| | | |
|---|---|---|
| 4,470,662 A | 9/1984 | Mumzhiu |
| 4,555,627 A | 11/1985 | McRae, Jr. |
| 4,656,641 A | 4/1987 | Scifres et al. |
| 4,737,028 A | 4/1988 | Smith |
| 4,745,276 A | 5/1988 | Broicher et al. |
| 4,772,789 A | 9/1988 | Maram et al. |
| 4,796,266 A | 1/1989 | Banwell et al. |
| 4,852,956 A | 8/1989 | Kramer |
| 4,871,916 A | 10/1989 | Scott |
| 5,005,934 A | 4/1991 | Curtiss |
| 5,050,176 A | 9/1991 | Naito et al. |
| 5,064,988 A | 11/1991 | E'nama et al. |
| 5,068,867 A | 11/1991 | Hasenberg et al. |
| 5,082,339 A | 1/1992 | Linnebach |
| 5,082,799 A | 1/1992 | Holmstrom et al. |
| 5,140,599 A | 8/1992 | Trutna, Jr. et al. |
| 5,161,408 A | 11/1992 | McRae et al. |
| 5,172,390 A | 12/1992 | Mooradian |
| 5,181,214 A | 1/1993 | Berger et al. |
| 5,225,679 A | 7/1993 | Clarke et al. |
| 5,255,073 A | 10/1993 | Wallin et al. |
| 5,264,368 A | 11/1993 | Clarke et al. |
| 5,315,436 A | 5/1994 | Lowenhar et al. |
| 5,331,651 A | 7/1994 | Becker et al. |
| 5,430,293 A | 7/1995 | Sato et al. |
| 5,457,709 A | 10/1995 | Capasso et al. |
| 5,491,714 A * | 2/1996 | Kitamura ............... 372/92 |
| 5,523,569 A | 6/1996 | Hornfeld et al. |
| 5,537,432 A | 7/1996 | Mehuys et al. |
| 5,656,813 A | 8/1997 | Moore et al. |
| 5,662,819 A | 9/1997 | Kadomura |
| 5,751,830 A | 5/1998 | Hutchinson |
| 5,752,100 A | 5/1998 | Schrock |
| 5,780,724 A | 7/1998 | Olender et al. |
| 5,824,884 A | 10/1998 | Olender et al. |
| 5,834,632 A | 11/1998 | Olender et al. |
| 5,854,422 A | 12/1998 | McKeon et al. |
| 5,862,162 A | 1/1999 | Maeda |
| 5,866,073 A | 2/1999 | Sausa et al. |
| 6,089,076 A | 7/2000 | Mueller et al. |
| 6,134,257 A | 10/2000 | Capasso et al. |
| 6,154,307 A | 11/2000 | Veronesi et al. |
| 6,157,033 A | 12/2000 | Chudnovsky |
| 6,192,064 B1 | 2/2001 | Algots et al. |
| 6,243,404 B1 | 6/2001 | Joyce |
| 6,326,646 B1 | 12/2001 | Baillargeon et al. |
| 6,327,896 B1 | 12/2001 | Veronesi et al. |
| 6,400,744 B1 | 6/2002 | Capasso et al. |
| 6,470,036 B1 | 10/2002 | Bailey et al. |
| 6,483,978 B1 | 11/2002 | Gao et al. |
| 6,553,045 B2 | 4/2003 | Kaspi |
| 6,575,641 B2 | 6/2003 | Yamabayashi et al. |
| 6,608,847 B2 * | 8/2003 | Wang et al. ............... 372/20 |
| 6,636,539 B2 | 10/2003 | Martinsen |
| 6,690,472 B2 | 2/2004 | Kulp et al. |
| 6,782,162 B2 | 8/2004 | Fukuzawa et al. |
| 6,803,577 B2 | 10/2004 | Edner et al. |
| 6,856,717 B2 | 2/2005 | Kilian |
| 6,859,481 B2 | 2/2005 | Zheng |
| 6,866,089 B2 | 3/2005 | Avila |
| 6,885,965 B2 | 4/2005 | Butler et al. |
| 6,909,539 B2 | 6/2005 | Korniski et al. |
| 6,995,846 B2 | 2/2006 | Kalayeh et al. |
| 7,032,431 B2 | 4/2006 | Baum et al. |
| 7,061,022 B1 | 6/2006 | Pham et al. |
| 7,088,076 B2 | 8/2006 | Densham et al. |
| 7,151,787 B2 | 12/2006 | Kulp et al. |
| 7,189,970 B2 | 3/2007 | Racca et al. |
| 7,265,842 B2 | 9/2007 | Paldus et al. |
| 7,345,277 B2 | 3/2008 | Zhang |
| 7,358,498 B2 | 4/2008 | Geng et al. |
| 7,424,042 B2 | 9/2008 | Day et al. |
| 7,429,734 B1 | 9/2008 | Tidwell |
| 7,466,734 B1 | 12/2008 | Day et al. |
| 7,492,806 B2 | 2/2009 | Day et al. |
| 7,535,656 B2 | 5/2009 | Day et al. |
| 7,535,936 B2 | 5/2009 | Day et al. |
| 7,590,316 B2 | 9/2009 | Dames |
| 7,623,234 B2 | 11/2009 | Puzey |
| 7,732,767 B2 | 6/2010 | Houde-Walter |
| 7,733,925 B2 | 6/2010 | Pushkarsky et al. |
| 7,755,041 B2 | 7/2010 | Killinger et al. |
| 7,796,341 B2 | 9/2010 | Day et al. |
| 7,818,911 B2 | 10/2010 | Houde-Walter et al. |
| 7,826,503 B2 | 11/2010 | Day et al. |
| 7,848,382 B2 * | 12/2010 | Weida et al. ............... 372/102 |
| 7,873,094 B2 | 1/2011 | Day et al. |
| 7,920,608 B2 | 4/2011 | Marsland, Jr. et al. |
| 2002/0024979 A1 | 2/2002 | Vilhelmsson et al. |
| 2002/0064198 A1 | 5/2002 | Koizumi |
| 2002/0090013 A1 | 7/2002 | Murry et al. |
| 2002/0105699 A1 | 8/2002 | Miracky et al. |
| 2002/0150133 A1 | 10/2002 | Aikiyo et al. |
| 2002/0176473 A1 | 11/2002 | Mooradian |
| 2003/0043877 A1 | 3/2003 | Kaspi |
| 2003/0063633 A1 | 4/2003 | Zhang et al. |
| 2003/0095346 A1 | 5/2003 | Nasu et al. |
| 2003/0123495 A1 | 7/2003 | Cox |
| 2003/0174315 A1 | 9/2003 | Byren et al. |
| 2003/0179789 A1 | 9/2003 | Pilgrim et al. |
| 2003/0198274 A1 | 10/2003 | Lucchetti |
| 2004/0013154 A1 | 1/2004 | Zheng |
| 2004/0032891 A1 | 2/2004 | Ikeda et al. |
| 2004/0095579 A1 | 5/2004 | Bisson et al. |
| 2004/0165640 A1 | 8/2004 | Clifford et al. |
| 2004/0208602 A1 | 10/2004 | Plante |
| 2004/0228371 A1 | 11/2004 | Kolodzey et al. |
| 2004/0238811 A1 | 12/2004 | Nakamura et al. |
| 2004/0264523 A1 | 12/2004 | Posamentier |
| 2005/0083568 A1 | 4/2005 | Nakae et al. |
| 2005/0105566 A1 | 5/2005 | Sacher |
| 2005/0199869 A1 | 9/2005 | Shi |
| 2005/0213627 A1 | 9/2005 | Masselink et al. |
| 2005/0237524 A1 | 10/2005 | Kamei |
| 2006/0056466 A1 | 3/2006 | Belenky et al. |
| 2006/0214107 A1 | 9/2006 | Mueller |
| 2006/0262316 A1 | 11/2006 | Baney |
| 2006/0268947 A1 | 11/2006 | Kalayeh |
| 2007/0019702 A1 | 1/2007 | Day et al. |
| 2007/0030865 A1 | 2/2007 | Day et al. |
| 2007/0047599 A1 | 3/2007 | Wysocki et al. |
| 2007/0195833 A1 * | 8/2007 | Nebendahl et al. ............. 372/20 |
| 2007/0291804 A1 | 12/2007 | Day et al. |
| 2008/0075153 A1 | 3/2008 | Day et al. |
| 2008/0231719 A1 | 9/2008 | Benson |
| 2008/0298406 A1 | 12/2008 | Day et al. |
| 2008/0304524 A1 | 12/2008 | Marsland et al. |
| 2009/0015914 A1 | 1/2009 | Duncan et al. |
| 2009/0159798 A1 | 6/2009 | Weida et al. |
| 2009/0213882 A1 | 8/2009 | Weida et al. |
| 2009/0257709 A1 | 10/2009 | Dames |
| 2009/0262768 A1 | 10/2009 | Day et al. |
| 2010/0110198 A1 | 5/2010 | Larson et al. |
| 2010/0132581 A1 | 6/2010 | Day et al. |
| 2010/0229448 A1 | 9/2010 | Houde-Walter et al. |
| 2010/0243891 A1 | 9/2010 | Day et al. |
| 2011/0006229 A1 | 1/2011 | Day et al. |

FOREIGN PATENT DOCUMENTS

| | | |
|---|---|---|
| EP | 0 877 454 A1 | 11/1998 |
| EP | 0 883 220 A2 | 12/1998 |
| EP | 2 081 265 A3 | 9/2009 |
| GB | 2286901 A | 8/1995 |
| JP | 55087107 A | 7/1980 |
| JP | 58072108 | 4/1983 |
| JP | 03-048480 A | 3/1991 |
| JP | 07-024322 B | 1/1995 |
| JP | 2005317819 A | 11/2005 |
| WO | WO9220127 A1 | 11/1992 |
| WO | WO 03/067720 A2 | 8/2003 |
| WO | WO2008036881 A2 | 3/2008 |
| WO | WO2008036884 A2 | 3/2008 |

OTHER PUBLICATIONS

Haim Lotem, Mode-hop suppression of Littrow grating-tuned lasers: comment, 20 Month 1994, p. 1, vol. 1, No. 00, Applied Optics (provided in parent U.S. Appl. No. 12/353,223).

Corrie David Farmer, "Fab and Eval. of QCL's", Sep. 2000, Faculty of Engineering, University of Glasgow, Glasgow, UK (provided in parent U.S. Appl. No. 12/353,223).

M. De Labachelerie and G. Passedat, Mode-hop suppression of Littrow grating-tuned lasers, Jan. 20, 1993, pp. 269-272vol. 32, No. 3, Applied OPtics, ® 1993 Optical Society of America (provided in parent U.S. Appl. No. 12/353,223).

S. Blaser et al., Alpes Lasers, Room-temperature continuous-wave single-mode quantum cascade lasers, Photonics West 2006, Novel In-Plane Semiconductors V:Quantum Cascade Lasers:6133-01 Switzerland (provided in parent U.S. Appl. No. 12/353,223).

Gaetano Scamarcio, Mid-IR and THz Quantum CAscade Lasers, 2005, Physics Dept., University of Bari, Bari Italy (provided in parent U.S. Appl. No. 12/353,223).

Gaetano Scamarcio et al., Micro-probe characterization of QCLs correlation with optical performance APL 78, 1177 & APL 78, 2095 (2001), APL 2002, APL 2004, University of Bari, Bari Italy (provided in parent U.S. Appl. No. 12/353,223).

J. Faist, THz and Mid-IR Quantum cascade lasers, QM in space, Chatillon, Mar. 31, Science 2002, University of Neuchatel, EU Projects Answer/Teranova; Agilent, Funding Swiss National Science Foundation (provided in parent U.S. Appl. No. 12/353,223).

Joel M. Hensley, Recent Updates in QCL-based Sensing Applications, Sep. 5-10, 2006, Physical Sciences, Inc., Andover, MA, 2nd International Workshop on Quantum Cascade Lasers, Ostuni, Italy (provided in parent U.S. Appl. No. 12/353,223).

J.M. Hensley et al., Demonstration of an External Cavity Terahertz Quantum Cascade Laser, Copyright 2005, Optical Society of America, Washington, DC 20036 (provided in parent U.S. Appl. No. 12/353,223).

L. Hildebrandt et al., Quantum cascade external cavity and DFB laser systems in the mid-infrared spectral range: devices and applications, 2004, Marburg Germany (provided in parent U.S. Appl. No. 12/353,223).

Richard Maulini et al., Broadly tunable external cavity quantum-cascade lasers, 2005, University of Neuchatel, Neuchatel Switzerland (provided in parent U.S. Appl. No. 12/353,223).

Tsekoun, A. et al; "Improved performance of QCL's through a scalable, manufacturable epitaxial-side-down mounting process"; Feb. 2006 (provided in parent U.S. Appl. No. 12/353,223).

Pushkarsky, M. et al.; "Sub-parts-per-billion level detection of NO2 using room temp. QCLs"; May 2006 (provided in parent U.S. Appl. No. 12/353,223).

Wirtz, D. et al.; "A tuneable heterodyne infrared spectrometer"; Physikalisches Institut; University of Koln; Koln Germany Spectrochimica 2002 (provided in parent U.S. Appl. No. 12/353,223).

Williams, B. et al.;"Terahertz QCLs and Electronics"; PhD-MIT 2003 (provided in parent U.S. Appl. No. 12/353,223).

Weida et al., Utilizing broad gain bandwidth in quantum cascade devices, Nov. 2010, vol. 49 (11) Optical Engineering, 111120, 0091-3286/2010 ©2010 SPIE.

Extended European Search Report for European Application No. 09150631.1, publication date Aug. 21, 2009, Daylight Solutions, Inc. (provided in parent U.S. Appl. No. 12/353,223).

Martini, Ranier et al.,"High duty cycle operation of quantum cascade lasers based on graded superlattice active regions," Journal of Applied Physics, Jun. 15, 2001, pp. 7735-7738,vol. 89, No. 12, XP012052642 ISSN:0021-8979, © 2001 American Institute of Physics (provided in parent U.S. Appl. No. 12/353,223).

Sitori, Carlo et al.,"Mid-Infrared (8.5 µm) Semiconductor Lasers Operating at Room Temperature," IEEE Photonics Technology Letters, Mar. 1997, pp. 297-299, vol. 9, No. 3, XP000684396, ISN:1041-1135, © 1997 IEE (provided in parent U.S. Appl. No. 12/353,223).

W.Y. Oh et al, "115 kHz tuning repetition rate ultrahigh-speed wavelength-swept semiconductor laser", Dec. 1, 2005, pp. 3159-3163, vol. 30, No. 23, Optics Letters, © 2005 Optical Society of America.

Weida et al.,"Tunable QC laser opens up mid-IR sensing applications," Jul. 2006, pp. 1-5, Laser Focus World, http://www.optoiq.com/index/photonics-technologies-applications/lfw-display/lfw-articles-tools-template/_pr . . . .

G.P. Luo et al.,Grating-tuned external-cavity quantum-cascade semiconductor lasers, May 7, 2001, Applied Physics Letters, vol. 78, No. 19, © 2001 American Institute of Physics (provided in parent U.S. Appl. No. 12/353,223) .

G. Wysocki et al.,Widely tunable mode-hop free external cavity quantum cascade laser for high resolution spectroscopic applications, Jul. 27, 2005, Applied Physics, B81, pp. 769-777, Applied Physics B Lasers and Optics (provided in parent U.S. Appl. No. 12/353,223).

Day et al., Miniaturized External Cavity Quantum Cascade Lasers for Broad Tunability in the Mid-Infrared, May 21, 2006, 1-55752-813-6, Lasers and Electro-Optics and 2006 Quantum Electronics and Laser Science Conference, © 2006 IEEE (provided in parent U.S. Appl. No. 12/353,223).

G. Totschig et al.,Mid-infrared external-cavity quantum-cascade laser XP-001161786, Oct. 15, 2002, pp. 1788-1790, Optics Letters/Vol. 27, No. 20, © 2002 Optical Society of America (provided in parent U.S. Appl. No. 12/353,223).

Thierry Aellen et al., Continuous-wave distributed-feedback quantum-cascade lasers on a Peltier cooler, Sep. 8, 2003, pp. 1929-1931, Applied Physics Letters, vol. 83, No. 10, © 2003 American Institute of Physics (provided in parent U.S. Appl. No. 12/353,223).

D. Weidmann et al., Development of a compact quantum cascade laser spectrometer for field measurements of Co 2 isotopes, Feb. 1, 2005, pp. 255-260, Applied PhysicsB, Lasers and Optics, Appl. Phys. B 80, published online: Sep. 29, 2004 © Springer-Verlag 2004 (provided in parent U.S. Appl. No. 12/353,223).

Cassidy et al., Short-external-cavity module for ehanced single-mode tuning of InGaAsP and AIGaAs semiconductor diode lasers, Oct. 1991, No. 10, pp. 2385-2388, © 1991 American Institute of Physics (provided in parent U.S. Appl. No. 12/353,223).

M.G. Littman, H.J. Metcalf: "Spectrally narrow pulse dye laser without beam expander" Applied Optics, vol. 17, No. 14, Jul. 15, 1978, pp. 2224-2227, XP002528173 US (provided in parent U.S. Appl. No. 12/353,223).

Patrick McNicholl and Harold J. Metcalf, Synchronous cavity mode and feedback wavelength scanning in dye laser oscillators with gratings, Sep. 1, 1985, pp. 2757-2761, vol. 24, No. 17, Applied Optics, © 1985 Optical Society of America (provided in parent U.S. Appl. No. 12/353,223).

Victor Rudometov and Eugene Rudometrov, Peltier Coolers, May 11, 2005, pp. 1-11, http://www.digit-life.com/article/peltiercoolers.com/ © Digit-Life.com 1997-2004.

T Topfer, KP Petrov, Y Mine, D Jundt, RF Curl, and FK Tittel, Room-temperature mid-infrared laser sensor for trace gas detection, Applied Optics, Oct. 20, 1997, pp. 8042-8049, vol. 36 No. 30, Oct. 20, 1997/Applied Optics.

Cavity Enhancing Sensors using QC Lasers, Jun. 7, 2005, pp. 1-6, http://www.infrared.phl.gov/enhanced.sensors.html, Webmaster: Pamela Kinsey, Reviewed: Nov. 23, 2004.

Transient FM Absorption Spectroscopy, Jun. 7, 2005, pp. 1 and 2, http://www.chem/tamu.edu/group/north/FM.html.

FM Spectoscopy With Tunable Diode Lasers, Application Note 7, pp. 1-10, New Focus Copyright 2001.

John Andrews and Paul Dalin,Frequency Modulation Spectroscopy, Dec. 2005, pp. 24-26, http://www.spectroscopyeurope.com.

R.F. Curl and F.K. Tittel,Tunable infrared laser spectroscopy, 1998, pp. 219-268, Annu. Rep. Prog-Chem. Sect. C, 2002.

Shawn Wehe et al., Aiaa 2002-0824 Measurements of Trace Pollutants in Combustion Flows Using Room-Temperature, Mid-IR Quantum Cascade Lasers , S. Wehe, et al. (Physical Sciences, Inc.) C Gmachi and F Capasso (Bell Lab., Lucent Technologies), Jan. 2002, cover and pp. 1-7, 40th AIAA Aerospace Sciences Meeting and Exhibit 14, Jan. 17, 2002, Reno, NV.

W. Huang, RRA Syms, J. Stagg and A.A. Lohmann, Precision MEMS Flxure mount for a Littman tunable external cavity laser, Mar. 2004, pp. 67-75, IEE Prc-Sci Meas. Technol vol. 151, No. 2 Mar. 2004.

K. Namjou, S. Cai, E.A. Whitaker, J. Faist, C. Gmacahi, F. Capasso, D.L. Sivco and A.Y. Cho, Sensitive absorption spectroscopy with a room-temperature distributed-feedback quantum-cascade laser, 1998, pp. 219-221, 1998 Optical Society of America.

Gregory E. Hall and Simon W. North, Transient Laser Frequency Modulation Spectroscopy, 2000, pp. 243-274, Annu. Rev.Phys. Chem. 2000.51:243-74-Copyright 2000.

External-cavity quantum-cascade lasers, May 11, 2005, pp. 1-4, http://www.unine.ch/phys/meso/EC/EC.html.

Frequency stabilization of diode lasers, May 30, 2005, pp. 1-17, Santa Chawla—National Physical Laboratory, http://www.ias.ac.in/currsci/jan25/articles41.htm, National Physical Lab, New Delhi 110 012 India.

R.A. Syms, A. Lohmann, Moems Tuning element for a Littrow External Cavity Laser, Dec. 2003, pp. 921-928, Journal of Microelectromechanical Systems, vol. 12, No. 6 Dec. 2003.

A.A. Koserev et al., Thermoelectrically cooled quantum cascade laser based sensor for continuous monitoring of ambient atmospheric CO—AA Koserev, FK Tettel, R Kohler, C Gmachi, F Capasso, DL Sivco, AY Cho, S Wehe and M Allen, 2002, cover and pp. 1-16, Copyright 2002 Optical Society of America.

European Patent Office Communication pursuant to Article 94(3) EPC for European Application No. 09150631.1, dated Feb .10, 2011, Daylight Solutions, Inc. (provided in parent U.S. Appl. No. 12/353-223).

File:LED, 5mm, green (en).svg-Wikipedia, the free encyclopedia, Description English: A labeled drawing of a 5mm round (the "normal" type) LED. Apr. 6, 2009, 3 pages, http://en.wikipedia.org/wiki/File:LED,_5mm,_green(en).svg.

Cooke, M., Producing more light than heat from quantum cascade lasers, published on-line Jan. 10, 2010, www.semiconductor-today.com, Semiconductor Today, vol. 5, Issue 1, pp. 106-107, Feb. 2010.

European Patent Office Communication pursuant to Article 94(3) for European Application No. 09150631.1 dated Feb. 10, 2011 (related to present application) Daylight Solutions, Inc.

Response to European Patent Office Communication dated Feb. 10, 2011 for European Application No. 09150631.1 as filed on Jun. 9, 2011 (related to present application) Daylight Solutions, Inc.

US 7,733,928, 06/2010, Marsland, Jr. et al. (withdrawn)

* cited by examiner

LASER SOURCE THAT GENERATES A PLURALITY OF ALTERNATIVE WAVELENGTH OUTPUT BEAMS

CROSS-REFERENCE TO RELATED APPLICATIONS

This application is a continuation of U.S. application Ser. No. 12/353,223 filed on Jan. 13, 2009, now U.S. Pat. No. 7,848,382 entitled "Laser Source that Generates a Plurality of Alternative Wavelength Output Beams" which is currently pending and claims priority on U.S. Provisional Application Ser. No. 61/021,854, filed Jan. 17, 2008, entitled "Laser Source and Gas Sensor System". As far as is permitted, the contents of U.S. application Ser. No. 12/353,223 and of U.S. Provisional Application Ser. No. 61/021,854 are incorporated herein by reference.

BACKGROUND

The usage, transportation, and storage of hazardous materials create many safety and environmental issues. More specifically, during usage, transportation, and storage of hazardous materials, leaks can release toxic or explosive gas into the surrounding environment. For example, industrial equipment used in the oil, gas, utility, and chemical industries can release toxic gas into the surrounding environment. As another example, hazardous gases can pose a threat to homeland security. In many cases, the hazardous gas is odorless, colorless, and spreads quickly. As a result thereof, it can be quite difficult to detect and locate the source of the leak.

Recently, it has been determined that laser sources that generate light in the mid infrared range ("MIR range") are particularly useful in absorption spectroscopy applications since many gases of interest have their fundamental vibrational modes in the MIR range, and thus present strong, unique absorption signatures within the MIR range. In order to detect a wide range of gases, the laser source must generate a set of sequential, specific output beams that span a portion or the entire the MIR range.

Unfortunately, emitting gases in many atmospheric environments are susceptible to intensity fluctuations due to air turbulence. This can make it very difficult to detect these emitting gases.

SUMMARY

The present invention is directed to a laser source for emitting a set of output beams, with each of the output beams in the set having a different center wavelength. In one embodiment, the laser source includes a gain medium, a feedback assembly and a control system. The gain medium includes a first facet, and the gain medium is adapted to generate a beam that exits the first facet. The feedback assembly includes a feedback device and a device mover. The feedback device is positioned in the path of the beam that exits the first facet and the feedback device redirects at least a portion of the beam back to the gain medium. The device mover continuously adjusts an angle of incidence of the beam on the feedback device. The control system selectively directs pulses of power to the gain medium as the device mover is continuously adjusting the angle of incidence.

In one embodiment, the laser source includes a position detector that generates a position signal that relates to the angle of incidence of the beam on the feedback device. In this embodiment, the control system can selectively direct the pulses of power to the gain medium based on the position signal from the position detector. For example, the position detector can include a plurality of encoder marks and an optical reader that monitors the encoder marks. In this embodiment, the control system can selectively direct a pulse of power to the gain medium whenever the optical reader reads a predetermined number of encoder marks. Further, the control system can determine a center wavelength of the output beam based on the position signal. With this design, the laser source rapidly and accurately generates one or more sets of sequential, wavelength specific output beams that span a predetermined detection range.

As provided herein, the gain medium can be a QC gain medium. In this embodiment, the gain medium can include a partly reflective second facet, and the output beams can exit the second facet. Further, the second facet can define a first end of an external cavity and the feedback device can defines a second end of the external cavity. With this design, the laser source can be extremely compact, hand-held, lightweight, stable, rugged, small, self-contained, and portable.

In certain embodiments, the feedback device includes a diffraction grating, and the device mover rapidly adjusts the angle of incidence of the beam on the diffraction grating. For example, the device mover can include a voice coil motor that quickly pivots the feedback device back and forth about a pivot axis. Alternatively, the device mover can include a rotary motor that rotates the diffraction grating about a rotation axis. Still alternatively, the feedback device can include a plurality of diffraction gratings, and the device mover can include a rotary motor that rotates the plurality of diffraction gratings about the rotation axis.

In yet another alternative embodiment, the feedback device includes a fixed diffraction grating, and one or more reflectors. In this embodiment, the device mover includes a rotary motor that rotates the one or more reflectors about a rotation axis.

As provided herein, the feedback device can be moved to a plurality of alternative device positions with the device mover. Further, the control system can direct a pulse of power to the gain medium at each of the plurality of device positions so that the laser source generates the set of output beams, with each of the output beams in the set having a different center wavelength.

Further, the position detector can generate a first position signal when the feedback device is at a first device position and a second position signal when the feedback device is at a second device position. In this embodiment, the control system can direct a pulse of power to the gain medium upon receipt of the first position signal, and the control system can direct another pulse of power to the gain medium upon receipt of the second position signal.

Additionally, the present invention is directed to a sensor system for imaging an emitting gas. For example, the imaging system can include an imager that captures a thermal image, and the laser source described above. In this embodiment, the set of output beams are directed at the emitting gas and one or more of the output beams are backscatter near and/or absorbed by the emitting gas. With this design, when a target emitting gas is present, the gas absorbs and attenuates the backscattered light. As a result thereof, a shadow or contrast that corresponds to the emitting gas is clearly visible in the image that is captured by the imager. In certain embodiments, because of the unique design disclosed herein, the sensor system is very accurate and can be extremely lightweight, stable, rugged, small, self-contained, and portable.

Additionally, the present invention is directed to one or more methods for generating a set of output beams.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

DESCRIPTION

Figure 1A:
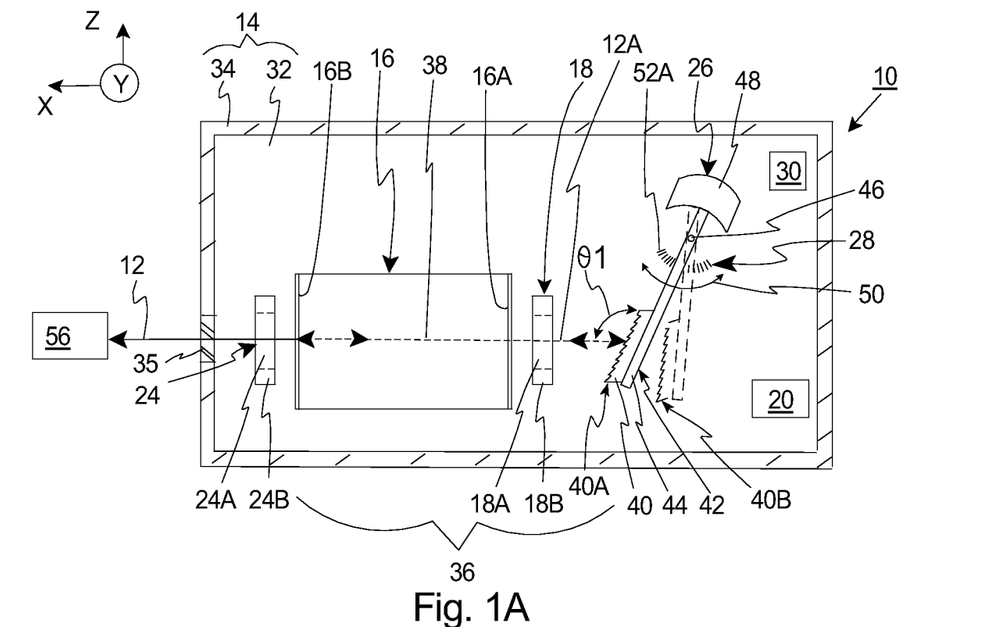
FIG. 1A is simplified top illustration in partial cut-away of a laser source having features of the present invention.
Figure 1B:
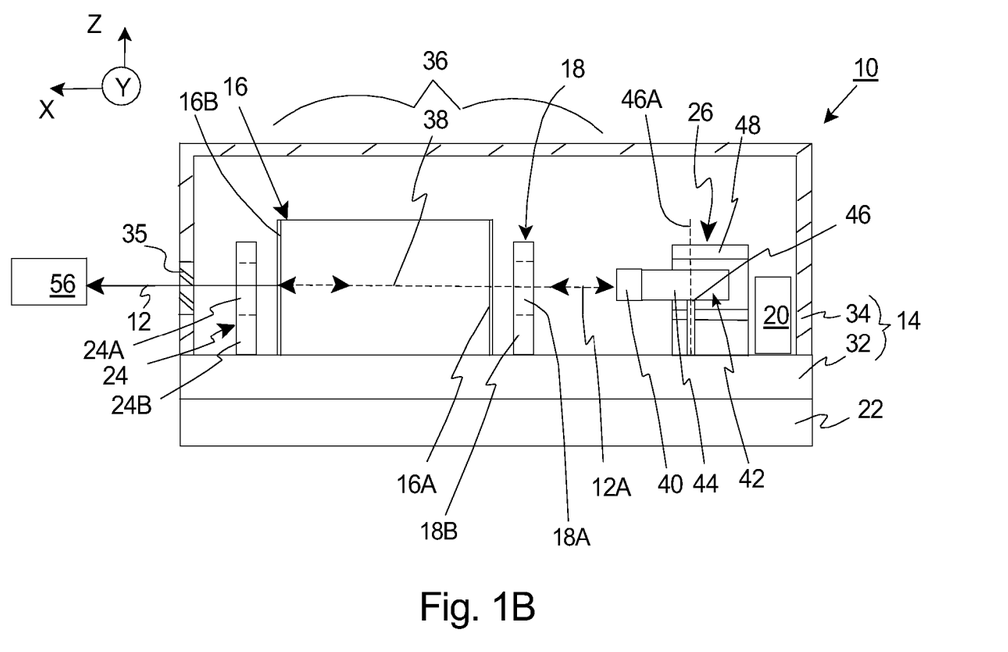
FIG. 1B is a simplified side illustration in partial cut-away of the laser source of FIG. 1B.

FIG. 1A is a simplified top illustration, in partial cut-away and FIG. 1B is a simplified side illustration, in partial cut-away of a laser source 10 that is suited for imaging, locating, detecting, and/or identifying an emitting gas (not shown in FIGS. 1A and 1B) and/or other industrial or testing applications. In one, non-exclusive embodiment, the laser source 10 is designed to rapidly and accurately generate one or more sets of sequential, wavelength specific output beams 12 that span a predetermined detection range. With this design, the set of output beams 12 from the laser source 10 can be specifically tailored to target the absorption features of the gases of interest. Further, in certain embodiments, because of the unique design disclosed herein, the laser source 10 can be extremely compact, hand-held, lightweight, stable, rugged, small, self-contained, and portable.

Moreover, in certain embodiments, the plurality of output beams 12 traverse the same optical path and originate from the same gain medium.

In one embodiment, the laser source 10 is a mid infrared ("MIR") laser source and the output beams 12 in the set have a center wavelength in the MIR range of approximately 2-20 micrometers. In this embodiment, the laser source 10 can be designed to generate the set of sequential, specific output beams 12 that span the entire or just a portion of the MIR range. These MIR laser sources 10 are particularly useful in absorption spectroscopy applications since many gases of interest have strong, unique absorption signatures within the MIR range. Alternatively, the laser source 10 can have generate one or more output beams 12 having a center wavelength of greater than or lesser than 2-20 micrometers.

A number of Figures include an orientation system that illustrates an X axis, a Y axis that is orthogonal to the X axis and a Z axis that is orthogonal to the X and Y axes. It should be noted that these axes can also be referred to as the first, second and third axes.

The design of the laser source 10 can be varied to achieve the desired type of gas detection or other usage of the laser source 10. In FIGS. 1A and 1B, the laser source 10 includes a source frame 14, a gain medium 16, a cavity optical assembly 18, a power source 20, a temperature controller 22, an output optical assembly 24, a wavelength dependant ("WD") feedback assembly 26, a position detector 28, and a laser control system 30 that cooperate to generate the one or more sets of output beams 12. The design of each of these components can be varied pursuant to the teachings provided herein. Further, it should be noted that the laser source 10 can be designed with more or fewer components than described herein.

The source frame 14 supports at least some of the components of the laser source 10. In one embodiment, (i) the gain medium 16, the cavity optical assembly 18, the output optical assembly 24, and the WD feedback assembly 26 are each fixedly secured, in a rigid arrangement to the source frame 14; and (ii) the source frame 14 maintains these components in precise mechanical alignment to achieve the desired wavelength of each of the output beams 12 of the set. Further, the laser control system 30, the power source 20, and the temperature controller 22 can be secured to source frame 14. With this design, all of the critical components are fixed to the source frame 14 in a stable manner, and the laser source 10 can be self-contained and extremely portable. Alternatively, for example, the power source 20, the temperature controller 22, and/or the laser control system 30 can be separate from and external to the source frame 14.

The design of the source frame 14 can be varied to achieve the design requirements of the laser source 10. In FIGS. 1A and 1B, the source frame 14 includes a rigid mounting base 32, a cover 34 that encloses the components of the laser source 10, and a window 35 that allows the output beam 12 to exit the cover 34. Alternatively, for example, the source frame 32 can be designed without the cover 34, without the window 35, and/or can have a configuration different from that illustrated in the Figures.

The mounting base 32 provides a rigid platform for fixedly mounting the gain medium 16, the cavity optical assembly 18, the output optical assembly 24 and the WD feedback assembly 26. In the Figures, the mounting base 32 is illustrated as being generally rectangular plate shaped. In one embodiment, the mounting base 32 is a single mechanical ground plane that provides structural integrity to the laser source 10. Alternatively, the mounting base 32 can have a configuration that is different than that illustrated in Figures.

In certain embodiments, the mounting base 32 is made of rigid material that has a relatively high thermal conductivity. In one non-exclusive embodiment, the mounting base 32 has a thermal conductivity of at least approximately 170 watts/meter K. With this design, in addition to rigidly supporting the components of the laser source 10, the mounting base 32 also readily transfers heat away from the gain medium 16 to the temperature controller 22. For example, the mounting base 32 can be fabricated from a single, integral piece of copper, copper-tungsten or other material having a sufficiently high thermal conductivity. The one piece structure of the mounting base 32 maintains the fixed relationship of the components mounted thereto and contributes to the small size and portability of the laser source 10.

In FIGS. 1A and 1B, the cover 34 is shaped somewhat similar to an inverted, open rectangular box. In one embodiment, the cover 34 is hermetically sealed to the mounting base 32 in an air tight manner. This allows the source frame 14 to provide a controlled environment around some of the components of the laser source 10. For example, the environment enclosed by the cover 34 can be filled with a fluid such as nitrogen or an air/nitrogen mixture to keep out moisture and humidity; or it can be subjected to a vacuum.

In certain embodiments, the overall size of the source frame 14 is relatively small so that the laser source 10 is very portability. For example, the source frame 14 can have dimensions of approximately 20 centimeters (height) by 20 centimeters (width) by 20 centimeters (length) (where length is taken along the propagation direction of the laser beam) or less, and more preferably, the source frame 14 has dimensions of approximately 3 centimeters (height) by 4 centimeters (width) by 5 centimeters (length). Still alternatively, the source frame 14 can have dimensions of less than approximately 10 millimeters (height) by 25 millimeters (width) by 30 millimeters.

The gain medium 16 generates the output beams 12. In one non-exclusive embodiment, the gain medium 16 is a semiconductor type laser that directly emits the output beams 12 without any frequency conversion. As used herein, the term semiconductor shall include any solid crystalline substance having electrical conductivity greater than insulators but less than good conductors.

In one embodiment, the gain medium 16 is a QC gain medium that is a unipolar semiconductor laser that includes a series of energy steps built into the material matrix while the crystal is being grown. With this design, electrons transmitted through the gain medium 16 emit one photon at each of the energy steps. In one embodiment, the QC gain medium 16 uses two different semiconductor materials such as InGaAs and AlInAs (grown on an InP or GaSb substrate for example) to form a series of potential wells and barriers for electron transitions. The thickness of these wells/barriers determines the wavelength characteristic of the gain medium 16. Fabricating QC gain medium of different thickness enables production of the laser having different output frequencies within the MIR range.

In the case of QC gain medium, the "diode" has been replaced by a conduction band quantum well. Electrons are injected into the upper quantum well state and collected from the lower state using a superlattice structure. The upper and lower states are both within the conduction band. Replacing the diode with a single-carrier quantum well system means that the generated photon energy is no longer tied to the material bandgap. This removes the requirement for exotic new materials for each wavelength, and also removes Auger recombination as a problem issue in the active region. The superlattice and quantum well can be designed to provide lasing at almost any photon energy that is sufficiently below the conduction band quantum well barrier.

As used herein the term QC gain medium shall also include Interband Cascade Lasers (ICL) in addition to Quantum Cascade type media. ICL lasers use a conduction-band to valence-band transition as in the traditional diode laser.

In FIGS. 1A and 1B, the gain medium 16 includes (i) a first facet 16A that faces the cavity optical assembly 18 and the WD feedback assembly 26, and (ii) a second facet 16B that faces the output optical assembly 24. In this embodiment, the QC gain medium 16 emits from both facets. In one embodiment, the first facet 16A is coated with an anti-reflection ("AR") coating and the second facet 16B is coated with a reflective coating. The AR coating allows light directed from the gain medium 16 at the first facet 16A to easily exit the gain medium 16 as a light beam 12A directed at the WD feedback assembly 26; and allows the light beam reflected from the WD feedback assembly 26 to easily enter the gain medium 16.

The output beams 12 exit from the second facet 16B and the plurality of output beams 12 travel the same optical path. The reflective coating on the second facet 16B reflects at least some of the light that is directed at the second facet 16B from the gain medium 16 back into the gain medium 16. In one non-exclusive embodiment, the AR coating can have a reflectivity of less than approximately 2 percent, and the reflective coating can have a reflectivity of between approximately 2-95 percent. In this embodiment, the reflective coating acts as an output coupler (e.g. a first end) for an external cavity 36.

In one non-exclusive embodiment, the QC gain medium 16 is approximately 2 millimeters by 0.5 millimeters, by 90 micrometers. A suitable QC gain medium 16 can be purchased from Alpes Lasers, located in Switzerland.

The gain medium 16 can generate quite a bit of heat. Accordingly, the temperature controller 22 can be an important component that is needed to remove the heat, thereby permitting long lived operation of the laser source 10 and consistent optical output power.

The cavity optical assembly 18 is positioned between the gain medium 16 and the WD feedback assembly 26 along a lasing axis 38 (along the X axis in FIGS. 1A and 1B), and collimates and focuses the light that passes between these components. For example, the cavity optical assembly 18 can include one or more lens 18A (illustrated in phantom), a lens mount 18B, and one or more lens fastener (not shown).

For example, the lens 18A can be an aspherical lens having an optical axis that is aligned with the lasing axis 38. In one embodiment, to achieve the desired small size and portability, the lens 18A has a relatively small diameter. In alternative, non-exclusive embodiments, the lens 18A has a diameter of less than approximately 5 or 10 millimeters, and a focal length of approximately 1, 2, 3, 4, 5, 6, 7, 8, 9, 10, 11, 12, 13, 14, 15, 16, 17, 18, 19, or 20 mm and any fractional values thereof. The lens 18A can comprise materials selected from the group of Ge, ZnSe, ZnS Si, CaF, BaF or chalcogenide glass. However, other materials may also be utilized. The lens may be made using a diamond turning or molding technique. The lens 18A can be designed to have a relatively large numerical aperture (NA). For example, the lens 18A can have a numerical aperture of at least approximately 0.6, 0.7, or 0.8. The NA may be approximated by the lens diameter divided by twice the focal length. Thus, for example, a lens diameter of 5 mm having a NA of 0.8 would have a focal length of approximately 3.1 mm.

The power source 20 provides electrical power to the gain medium 16, the laser electronic controller 30, and the temperature controller 22. In FIGS. 1A and 1B, the power source 20 is a battery that is secured to the source frame 14. For example, the battery can be nickel metal hydrate. Alternatively, the power source 20 can be external to the source frame 14. For example, the power source 20 can be an external battery or a power outlet.

The temperature controller 22 can be used to control the temperature of the gain medium 16, the mounting base 32, and/or one or more of the other components of the laser source 10. Further, by controlling the temperature, the temperature controller 22 can be used to maintain the relative position of the gain medium 16, the optical assemblies 18, 24 and the WD feedback assembly 26.

In one embodiment, the temperature controller 22 includes a thermoelectric cooler and a temperature sensor (not shown). The thermoelectric cooler may be controlled to effect cooling or heating depending on the polarity of the drive current thereto. In FIGS. 1A and 1B, the thermoelectric cooler is fixed to the bottom of the mounting base 32 so that the thermoelectric cooler is in direct thermal communication with the mounting base 32, and so that the thermoelectric cooler can provide additional rigidity and support to the mounting base 32. In one embodiment, the top of the thermoelectric cooler is approximately the same size as the bottom surface of the mounting base 32. This promotes good heat transfer between the thermoelectric cooler and the mounting base 32, and maximizes the support for the mounting base 32 provided by the thermoelectric cooler. The thermoelectric cooler can be fixedly secured to the mounting base with bolts, epoxy, welding, solder or other suitable means.

Alternatively, an intermediate plate may be attached between the thermoelectric cooler and the mounting base 32.

The temperature sensor provides temperature information that can be used to control the operation of the thermoelectric cooler so that the thermoelectric cooler can maintain the desired temperature of the laser source 10. The temperature sensor can be positioned on the mounting base near the gain medium 16 and can be used to monitor the temperature of the gain medium 16.

It should be noted that fine tuning of the output beams 12 can be achieved by controlling the temperature of the gain medium 16, such as by changing the DC bias current. Such temperature tuning is relatively narrow and may be used to vary the wavelength by approximately 1-2 gigahertz/Kelvin which is typically less than 0.01% of the peak emission wavelength.

Additionally, or alternatively, the source frame 14 can be mounted to a heat sink (not shown) inside a larger housing (not shown) which may also contain additional equipment including cooling fans and vents to further remove the heat generated by the operation of the laser source 10.

The output optical assembly 24 is positioned between the gain medium 16 and the window 35 in line with the lasing axis 38. In this design, and the output optical assembly 24 collimates and focuses the output beams 12 that exit the second facet 16B of the gain medium 16. For example, the output optical assembly 24 can include one or more lens 24A (illustrated in phantom), a lens mount 24B, and a lens fastener. The lens 24A of the output optical assembly 24 can be somewhat similar in design to the lens 16A of the cavity optical assembly 16.

The WD feedback assembly 26 reflects the light back to the gain medium 16, and is used to precisely select and adjust the lasing frequency of the external cavity 36 and the wavelength of the output beam 12. Stated in another fashion, the WD feedback assembly 26 is used to feed back to the gain medium 16 a relatively narrow band wavelength which is then amplified in the gain medium 16. In this manner, the output beam 12 may be tuned with the WD feedback assembly 26 without adjusting the gain medium 16. Thus, with the external cavity 36 arrangements disclosed herein, the WD feedback assembly 26 dictates what wavelength will experience the most gain and thus dominate the wavelength of the output beam 12.

A number of embodiments of the WD feedback assembly 26 are described below. In these embodiments, the WD feedback assembly 26 is spaced apart from the gain medium 16 and defines a second end of the external cavity 36. In this embodiment, the external cavity 36 extends from the output coupler (reflective coating) on the second facet 16B to the WD feedback assembly 26. The term external cavity 36 is utilized to designate the WD feedback assembly 26 is positioned outside of the gain medium 16. In FIGS. 1A and 1B, the external cavity 36 is not external to the source frame 14 in which the gain medium 16 is contained.

In FIGS. 1A and 1B, the WD feedback assembly 26 includes a feedback device 40 and a feedback mover 42 that cooperate to rapidly adjust the lasing frequency of the external cavity 36 and the wavelength of each of the sequential output beams 12.

In one embodiment, the feedback device 40 is a diffraction grating that has wavelength dependent reflectivity, and rotation of the diffraction grating relative to the lasing axis 38 and the gain medium 16 with the feedback mover 42 adjusts the lasing wavelength and the wavelength of the output beam 12. A typical diffraction grating 40 includes a glass or polished metal reflector surface having a large number of very fine parallel grooves or slits. With this design, rotation of the grating 40 relative to the gain medium 16 and the incident beam 12A changes an angle of incidence $\theta$ of the beam 12 onto the feedback device 40 and the wavelength of the output beam 12. In this embodiment, changing the incidence angle $\theta$ serves to preferentially select a single wavelength which is the first order diffracted light from the grating 40. Thus, the grating 40 is used to precisely adjust the lasing frequency of the external cavity 36 and the wavelength of the output beam 12. Stated in another fashion, the grating 40 is used to feed back to the gain medium 16 a relatively narrow band wavelength which is then amplified in the gain medium 16.

In FIG. 1A, the feedback device 40 is illustrated in a first device position 40A having a first angle of incidence $\theta 1$, and a second device position 40B (illustrated in phantom) having a second angle of incidence $\theta 2$ (illustrated in FIG. 4B) that is different than the first angle of incidence $\theta 1$. When the feedback device 40 is in the first device position 40A, the laser 10 generates a first output beam having a first center wavelength; and when the feedback device 40 is in the second device position 40B, the laser 10 generates a second output beam having a second center wavelength that is different from the first center wavelength. The difference in wavelength between the first output beam and the second output beam will depend upon the difference between the first angle of incidence $\theta 1$ and the second angle of incidence $\theta 2$.

In alternative, non-exclusive embodiments, the feedback device 40 can be moved to control the fixed center wavelength of each output beam 12 to within approximately 0.1, 0.01, 0.001, or 0.0001 micrometers. In certain embodiments, with the designs provided herein, each of output beams 12 has a relatively narrow line width. In non-exclusive examples, the laser source 10 can be designed so that the line width of the output beams 12 is less than approximately 5, 4, 3, 2, 1, 0.8, 0.5, or 0.1 cm-1. Alternatively, the laser source 10 can be designed so that the line width of the output beams 12 is greater than approximately 7, 8, 9, or 10 cm-1. The spectral width of the output beams 12 can be adjusted by adjusting the cavity parameters of the external cavity 36. For example, the spectral width of the output beams 12 can be increased by increasing the focal length of the cavity optical assembly 18.

Alternatively, for example, the feedback device 40 can include a MEMS grating.

The feedback mover 42 rapidly and continuously adjusts the angle of incidence $\theta$ of the beam 12A on the feedback device 40 to quickly generate the set of output beams. In FIGS. 1A and 1B, the feedback mover 42 includes a mover arm 44, an arm pivot 46, and a motor 48. In this embodiment, the mover arm 44 is a generally rigid beam that includes a distal end that retains the grating 40 and a proximal end that is secured to the motor 48. Further, the arm pivot 46 pivotable connects (via one or more bearings) the mover arm 44 to the mounting base 32 intermediate the distal end and proximal end of the mover arm 44 so that the grating 40 pivots about a pivot axis 46A. Moreover, the motor 48 can be a voice coil type actuator that quickly pivots and moves the mover arm 44 (as illustrated by arrow 50 in FIG. 1A) and the grating 40 about the pivot axis 46A. The voice coil type actuator is mechanically durable, very fast, and highly accurate. Alternatively, the motor 48 can be another type of actuator that fits these design requirements.

With the design illustrated in FIGS. 1A and 1B, the tuning of the wavelength of the output beams 12 is realized by changing the angle of incidence θ of the grating 40 (by pivoting the grating 40 about the pivot axis 46A) to change the lasing wavelength. Thus, in FIGS. 1A and 1B, the angle of incidence θ is changed by changing the angle of the feedback element 40 relative to the incident beam 12A. Stated in another fashion, the motor 48 can move the feedback device 40 to a plurality of alternative device positions 40A, 40B (only two are illustrated in FIG. 1) to adjust the angle of incidence θ.

In certain designs, in order to realize the full tuning range of the laser 10, the grating 40 must be rotated over an adjustment range that is approximately five degrees. Thus, in this embodiment, the motor 48 adjusts the angle of incidence θ and the angle of the grating 40 approximately five degrees to generate the desired set of output beams 12. In alternative embodiments, the motor 48 can be designed so that the adjustment range of the angle of incidence θ is approximately two, three, four, six, seven, eight, nine or ten degrees.

In many spectroscopic applications, it is desirable to tune over the entire range of the laser 10 in a time that is short compared to the environment being evaluated. For example, if the laser 10 is used to target gases in the open air, the target gases are susceptible to intensity fluctuations due to atmospheric turbulence. In order to approximately "freeze" the atmosphere and acquire a spectrum with a substantially unvarying intensity profile, it is necessary to scan the laser 10 faster than the atmospheric turbulence.

As non-exclusive examples, with the designs provided herein, the motor 48 moves the grating 40 to adjust the angle of incidence θ over the entire adjustment range to generate the spectrum of output beams 12 in less than approximately one, two, three, four, five, seven or ten milliseconds. Thus, the motor 48 allows for rapid sweeps across the wavelength range of the laser 10. This is necessary to acquire a complete molecular spectrum before the measurement volume significantly changes due to conditions such as atmospheric turbulence.

The position detector 28 accurately measures and monitors the position of at least a portion of the WD feedback assembly 26 and provides a position signal to the control system 30 that relates to the position of at least a portion of the WD feedback assembly 26. Stated in another fashion, the position detector 28 can generate a position signal that relates to each position of the moving feedback device 40. For example, the position detector 28 can generate a first position signal when the feedback device 40 is at the first device position 40A and a second position signal when the feedback device 40 is at the second device position 40B. Further, the position signals relate to the angle of incidence θ of the beam 12A on the feedback device 40. As non-exclusive examples, the position detector 28 can be an optical encoder, or a Hall type sensor.

In one non-exclusive example, the position detector 28 is an optical encoder that includes a plurality of encoder marks 52A on the mounting base 32, and an optical reader 52B (illustrated in FIGS. 4A and 4B in phantom) that is secured to the mover arm 44. With this design, the optical reader 52B can monitor the encoder marks 52A and provide a position signal that relates to the position of the mover arm 44 and the grating 40 as the mover arm 44 and the grating 40 are being moved relative to the incident beam 12A.

The control system 30 controls the operation of the laser source 10 including the electrical power to the device mover 42, the electrical power that is directed to the gain medium 16 (e.g. controls the gain medium 16 by controlling the electron injection current), and the temperature controller 22. For example, the control system 30 can include one or more processors. In FIGS. 1A and 1B, the control system 30 is rigidly and fixedly mounted to the source frame 14 so that the laser source 10 is portable and rugged. Alternatively, for example, the control system 30 can be external to the source frame 14.

In FIGS. 1A and 1B, the control system 30 receives the position signals from the position detector 28 and directs power to the motor 48 to continuously move the grating 40 back and forth about the pivot axis 46A over the entire adjustment range of the grating 40.

Further, the control system 30 can direct power to the gain medium 16 in a fashion that minimizes heat generation in, and power consumption of the gain medium 16 while still achieving the desired set of output beams 12. For example, to realize low power consumption, the power to the gain medium 16 can be pulsed on and off. Pulsing of the power to the gain medium 16 not only reduces power consumption, it also reduces the thermal load produced by the laser 10, and allows higher temperature operation such that more efficient above-ambient temperature control can be used to stabilize the laser 10. The benefits of running the laser 10 in pulsed mode extend to a reduction in size and complexity due to the simpler and more robust above-ambient temperature control and battery operation. This in turn aids in creating a truly portable laser 10 by reducing the size and weight, and enabling cordless battery operation. It also enables more compact and rugged lasers 10 to be built that can be field-deployed.

The collection of accurate spectra requires that the wavelength of the output beam 12 be precisely known as the laser 10 is tuned. In certain embodiments, the control system 30 directs the pulses of power to the gain medium 16 based on the position signal received from the position detector 28. In this example, the control system 30 can direct a pulse of power to the gain medium 16 every time the optical reader 52B reads a predetermined number of encoder marks 52A. For example, the predetermined number can be one, two, or three encoder marks 52A.

Stated in another fashion, the control system 30 can direct a pulse of power to the gain medium 16 at each of the plurality of device positions 40A, 40B (only two are shown) so that the laser source 10 generates the set of output beams 12. In this embodiment, the control system 30 can direct a pulse of power to the gain medium upon receipt of each new position signal. As a result thereof, the specific wavelength of the output beams 12 will not be influenced by variations in speed of the motor 48.

In one embodiment, the pulsing of the power to the gain medium 16 allows the laser pulses to be tied directly to the angular rotation by employing a phase-locked-loop (PLL) technique where the position signals from the position detector 28 are up-converted in frequency and phase locked to the angular signals to allow the pulses of power to be fired at precise angular increments that are well characterized. These angles for each power pulse can then be converted to an accurate wavelength scale for the recorded chemical spectra.

Accuracy and sensitivity are also enabled by using boxcar integration techniques with the position signals to allow the high-frequency pulsing of the laser to be analyzed in real time. This is necessary to use the full spectral range of the laser even as it is rapidly tuning.

In one non-exclusive embodiment, the control system 30 can control the motor 48 and the gain medium 16 to generate a set of sequential, specific, different wavelength output beams 12 that span a portion or the entire the MIR range. In one non-exclusive example, the motor 48 and the gain medium 16 can be controlled by the control system 30 to sequentially generate approximately one thousand different wavelength output beams 12 that cover a detection range of approximately four to six micrometers (4 to 6 micrometers). In another non-exclusive example, the motor 48 and the gain medium 16 can be controlled by the control system 30 to sequentially generate more than one thousand or fewer than one thousand different wavelength output beams 12 and the detection range can be greater or less than six micrometers. For example, in yet another non-exclusive example, the motor 48 and the gain medium 16 can be controlled by the control system 30 to sequentially generate five hundred different wavelength output beams 12 that cover the detection range of approximately two micrometers.

In certain designs, utilization of the whole spectral range of the laser 10 is necessary to achieve specificity when analyzing mixtures of chemicals. The greater the spectral range that can be analyzed enhances resolution between different spectral signatures for different chemicals, thus allowing the individual components to be detected.

In certain embodiments, in order to achieve good contrast in the captured image, is may be necessary to generate an output beam 12 having a peak optical power of greater than approximately 1 milliwatt. Further, in certain embodiments, an even better contrast can be achieved with an output beam 12 having a peak optical power greater than approximately 100 milliwatts.

The duration of each pulse of power directed by the control system 30 to the gain medium can also be varied. In alternative, non-exclusive embodiments, control system 30 can control each pulse of power to have a duration of approximately 10, 25, 50, 75, 100, 150, 200, 300, 400, 500, 600 or 700 nanoseconds.

Additionally, the laser source 10 can be calibrated using a wavelength measurement device 56 during manufacturing of the laser source 10. More specifically, with the laser source 10 activated, the device mover 42 can be used to change the angle of incidence θ, while monitoring position of the feedback device 40 with the position detector 28, and wavelength of the output beams 12 with the wavelength measurement device 56. With this design, each position signal of the position detector 28 can be corresponded to a measured center wavelength of one of the output beams 12 of the set. Stated in another fashion, the control system 30 can determine a center wavelength of the output beam 12 based on the position signal.

Figure 2:
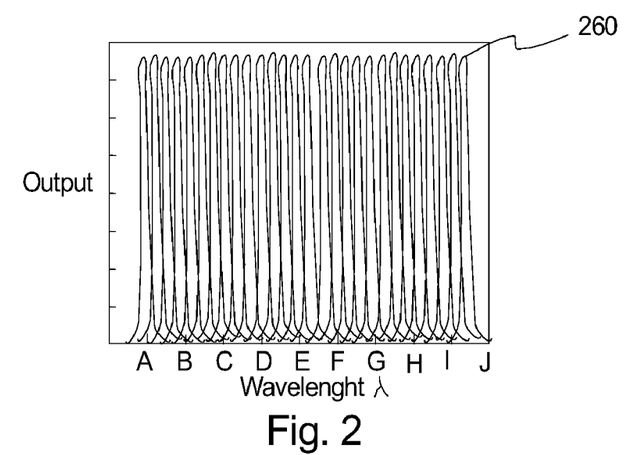
FIG. 2 is a simplified graph that illustrates a center wavelength for a set of output beams.

FIG. 2 is a simplified graph that illustrates the wavelengths of a set 260 of output beams that can be generated by the laser source 10 (illustrated in FIGS. 1A and 1B). For example, the laser source 10 can be controlled to generate the set 260 of sequential, specific, different center wavelength output beams that span a predetermined range. In this embodiment, after generating the set 260 of output beams, an imaging system (not shown in FIG. 2) can analyze the information to identify the gases detected and/or how much of each of the gases is present.

Figure 3A:
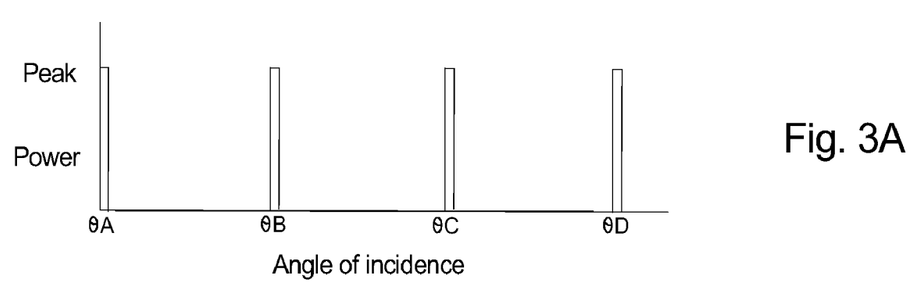
FIG. 3A is a graph that illustrates pulses of power directed to a gain medium versus angle of incidence.

FIG. 3A is a graph that illustrates power directed to the gain medium 16 (illustrated in FIGS. 1A and 1B) by the control system 30 (illustrated in FIGS. 1A and 1B) versus angle of incidence. In this example, the control system 30 pulses the power (as opposed to constant power) directed to the gain medium 16 when the position detector determines that the angle of incidence θ is equal to A, B, C, or D. In one non-exclusive example, the control system 30 generates approximately 1 to 100 milliwatts optical power peak for a relatively short period of time (e.g. 100-200 nanoseconds), and the control system 30 directs low or no power to the gain medium 16 between the peaks.

With this design, relatively high power is directed to the gain medium 16 for short, spaced apart periods of time. As a result thereof, the gain medium 16 lases with little to no heating of the core of the gain medium 16, the average power directed to the gain medium 16 is relatively low, and the desired optical power of the output beam 12 can be efficiently achieved. It should be noted that as the temperature of the gain medium 16 increases, the efficiency of the gain medium 16 decreases. With this embodiment, the pulsing of the gain medium 16 keeps the gain medium 16 operating efficiently and the overall system utilizes relatively low power. As a result thereof, the laser source 10 can be battery powered.

Figure 3B:
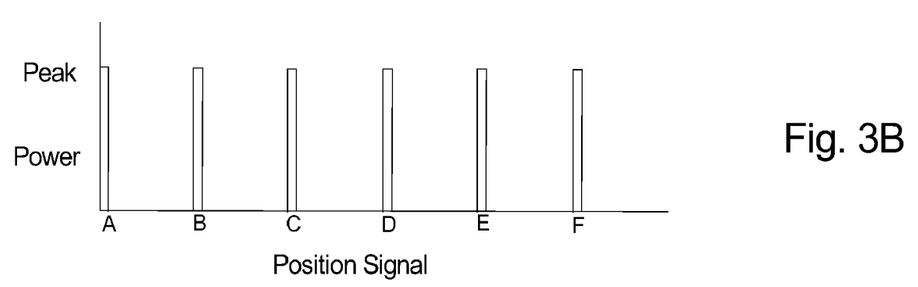
FIG. 3B is a graph that illustrates pulses of power directed to a gain medium versus position signals.

FIG. 3B is another example of how power can be directed to the gain medium. More specifically, FIG. 3B is a graph that illustrates power directed to the gain medium 16 (illustrated in FIGS. 1A and 1B) by the control system 30 (illustrated in FIGS. 1A and 1B) versus position signal. In this example, the control system 30 pulses the power directed to the gain medium 16 when the position detector determines that the position signal is equal to A, B, C, D, E, or F. In one non-exclusive example, the control system 30 again generates approximately 1 to 100 milliwatts optical power peak for a relatively short period of time (e.g. 100-200 nanoseconds), and the control system 30 directs low or no power to the gain medium 16 between the peaks.

Figure 3C:
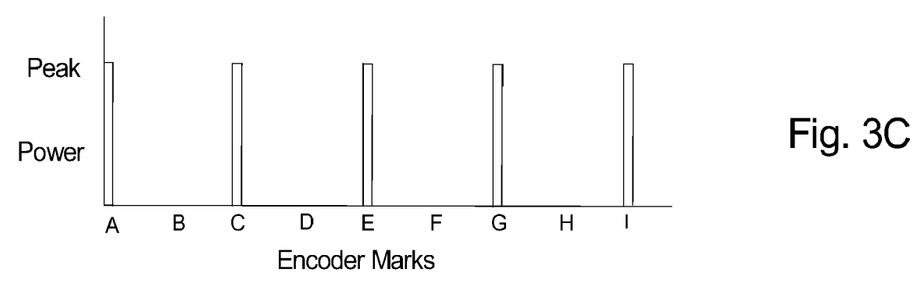
FIG. 3C is a graph that illustrates pulses of power directed to a gain medium versus number of encoder marks.

FIG. 3C is yet another example of how power can be directed to the gain medium. More specifically, FIG. 3C is a graph that illustrates power directed to the gain medium 16 (illustrated in FIGS. 1A and 1B) by the control system 30 (illustrated in FIGS. 1A and 1B) versus encoder marks. In this example, the control system 30 pulses the power directed to the gain medium 16 when the position detector determines that the encoder marks is equal to A, C, E, G, or I. Stated in another fashion, the control system 30 can direct a pulse of power to the gain medium 16 every time the optical reader 52B reads a predetermined number of encoder marks 52A. In FIG. 3C, the predetermined number is two encoder marks 52A. In this design, the time between the pulses represents the time it takes to move the grating 40 two encoder marks 52A.

In one non-exclusive example, the control system 30 again generates approximately 1 to 100 milliwatts optical power peak for a relatively short period of time (e.g. 100-200 nanoseconds), and the control system 30 directs low or no power to the gain medium 16 between the peaks.

Figure 4A:
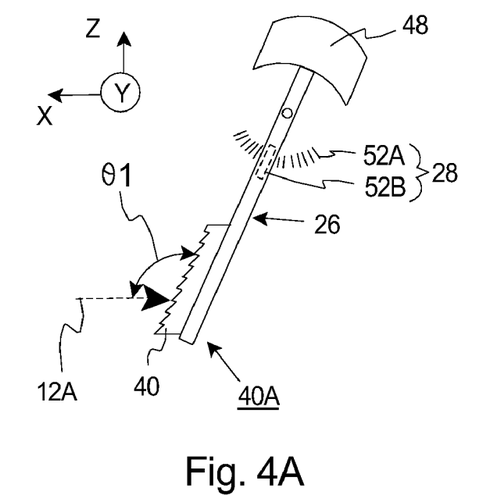
FIG. 4A is a simplified illustration of a position detector and a feedback assembly having features of the present invention in a first device position.
Figure 4B:
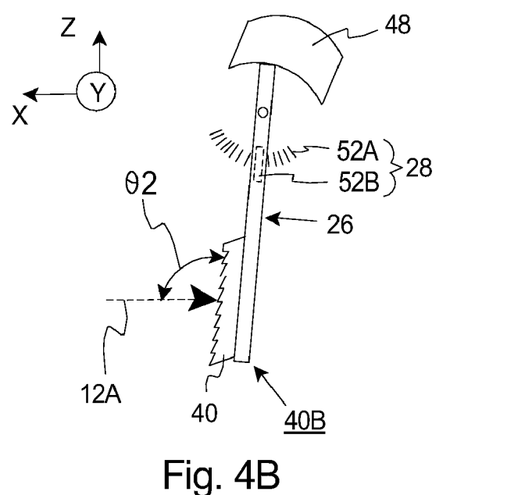
FIG. 4B is a simplified illustration of the position detector and the feedback assembly of FIG. 4A in a second device position.
Figure 5A:
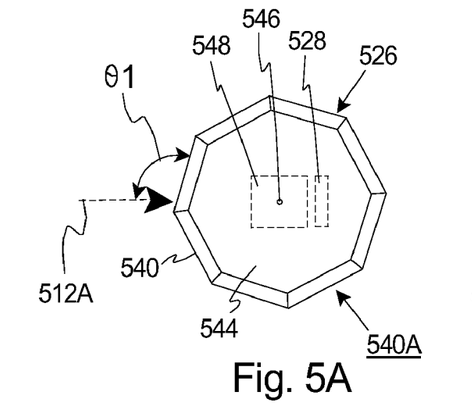
FIG. 5A is a simplified illustration of another embodiment of a position detector and a feedback assembly having features of the present invention in a first device position.
Figure 5B:
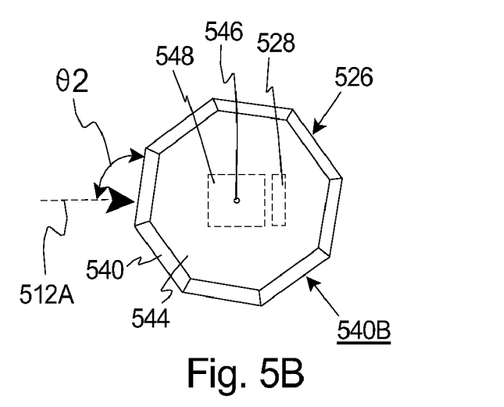
FIG. 5B is a simplified illustration of the position detector and the feedback assembly of FIG. 5A in a second device position.

FIG. 4A is a simplified illustration of the WD feedback assembly 26 of FIGS. 1A and 1B in the first device position 40A and the first angle of incidence θ1, and FIG. 4B illustrates the WD feedback assembly 26 in the second device position 40B and the second angle of incidence θ2. These Figures also illustrate the beam incident 12A on the WD feedback assembly 26, and the encoder marks 52A and the optical reader 52B of the position detector 28. In this embodiment, the motor 48 has moved the grating 40 between the two positions 40A, 40B FIG. 5A is a simplified illustration of another embodiment of a WD feedback assembly 526 in a first device position 540A and the first angle of incidence θ1, and FIG. 5B illustrates the WD feedback assembly 526 in a second device position 540B and the second angle of incidence θ2. The beam 512A incident on the WD feedback assembly 526 is also illustrated in these Figures. In this embodiment, the WD feedback assembly 526 includes a plurality of feedback devices 540 (i.e. diffraction gratings), a multiple sided device housing 544 that retains the feedback devices 540, and a rotary motor 548 (illustrated as a box in phantom) that rotates the devices 540 and the device housing 544 about a rotation axis 546.

The number of feedback devices 540 used in this design can be varied. For example, in FIGS. 5A and 5B, the WD feedback assembly 526 includes eight diffraction gratings 540 and the device housing 544 is octagonal shaped. Alternatively, this WD feedback assembly 526 can include more than eight or fewer than eight gratings 540. Generally speaking, as the number of gratings 540 is increased, the number of spectral sweeps per motor revolution is increased. As another example, the WD feedback assembly 526 could be designed with a single grating 540. However, in this design, the laser may only tuned over a five degree once per revolution of the grating 540. This leads to a relatively low duty cycle for laser scanning.

In one embodiment, the rotary motor 548 is a brushless DC servo motor. This type of motor is capable of (i) highly linear rotation, (ii) rotation speeds allowing one millisecond and faster scans over five degrees of grating rotation, and (ii) continuous operation with lifetimes of several years.

In this embodiment, the control system (not shown in FIGS. 5A and 5B) again receives position signals from the position sensor 528 (illustrated as a box in phantom). Further, the control system can direct power pulses to the gain medium (not shown in FIGS. 5A and 5B) at certain position signals, and not when the gratings 540 are at non-useful angles.

Figure 6A:
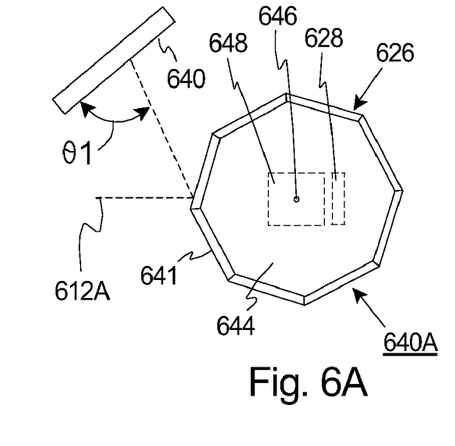
FIG. 6A is a simplified illustration of still another embodiment of a position detector and a feedback assembly having features of the present invention in a first device position.
Figure 6B:
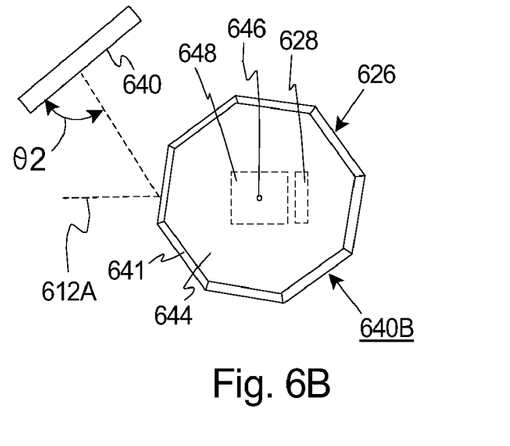
FIG. 6B is a simplified illustration of the position detector and the feedback assembly of FIG. 6A in a second device position.

FIG. 6A is a simplified illustration of another embodiment of a WD feedback assembly 626 in a first device position 640A and the first angle of incidence θ1, and FIG. 6B illustrates the WD feedback assembly 626 in a second device position 640B and the second angle of incidence θ2. The beam incident on the WD feedback assembly 626 is also illustrated in these Figures. In this embodiment, the WD feedback assembly 626 includes a single stationary feedback device 640 (i.e. a grating), plurality of reflectors 641 (i.e. mirrors), a multiple sided device housing 644 that retains the reflectors 641, and a rotary motor 648 (illustrated as a box in phantom) that rotates the reflectors 641 and the device housing 644 about a rotation axis 646. In this embodiment, the reflectors 641 sequentially direct the intracavity laser beam 612A at the fixed grating 640. This design may be preferred over the embodiment illustrated in FIGS. 5A and 5B, since it may be easier to make a multi-faceted mirror than to align and attach multiple gratings to the device housing.

The number of mirrors 641 used in this design can be varied. For example, in FIGS. 6A and 6B, the WD feedback assembly 626 includes eight mirrors 641 and the device housing 644 is octagonal shaped. Alternatively, this WD feedback assembly 626 can include more than eight or fewer than eight mirrors 641.

In this embodiment, the rotary motor 648 can again be a brushless DC servo motor. Further, in this embodiment, the control system (not shown in FIGS. 6A and 6B) again receives position signals from the position sensor 628 (illustrated as a box in phantom). Further, the control system can direct power pulses to the gain medium (not shown in FIGS. 6A and 6B) at certain position signals, and not when the mirrors 641 are at non-useful angles.

Figure 7:
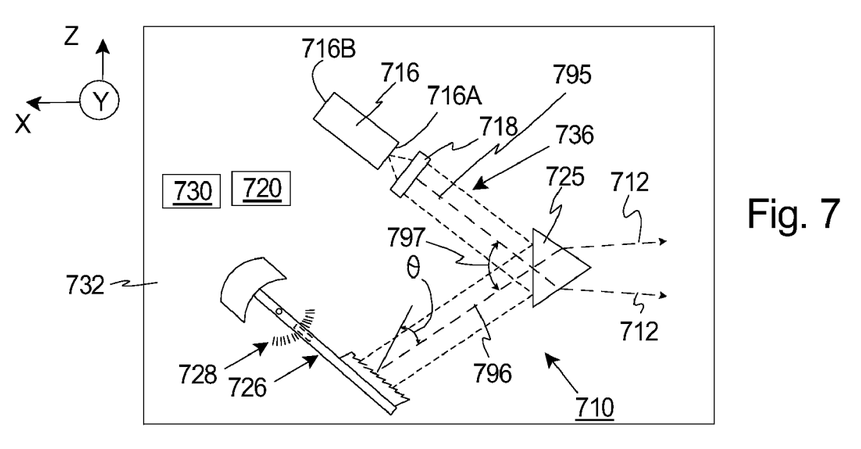
FIG. 7 is a simplified illustration of another embodiment of a laser source having features of the present invention.

FIG. 7 is a simplified illustration of another embodiment of a laser source 710 that is somewhat similar to the laser source 10 described above. In this embodiment, the laser source 710 includes a gain medium 716, a cavity optical assembly 718, a power source 720, a control system 730, a mounting base 732, a wavelength dependant ("WD") feedback assembly 726, and a position detector 728 that are somewhat similar to the corresponding components described above. However, in this embodiment, the gain medium 716 emits from only a first facet 716A which is coated with an anti-reflection (AR) coating, a second facet 716B of the gain medium 716 is coated with a high reflection (HR) coating, and the external cavity 736 is folded. Further, in this embodiment, the laser source 710 includes a beam reflector 725 that directs a portion of the beam towards the WD feedback assembly 726 and allows a portion of the beam to pass there through as the output beam 712.

In this embodiment, the beam reflector 725 is a partly reflective output coupler that reflects a portion of the beam and allows a portion of the beam to transmit there through. In this design, the degree of reflectively of the beam reflector 725 can be adjusted to optimize the output beam 712. Stated in another fashion, the degree of reflectivity of the beam reflector 725 is optimized to optimize the tuning range and power of the laser source 710. In one embodiment, the beam reflector 725 is a prism that requires only a coating on the surface that faces the gain medium 716. This is because the residual reflection on the other surfaces of the prism will not feed back into the laser cavity 736. It should be noted that in certain designs that the beam reflector 725 naturally produces two output beams 712. Because many applications rely on picking off some of the output beam 712 to use for a reference channel, the two exiting beams 712 (having the same wavelength) allows a reference channel to be implemented without the inclusion of an additional beam splitter.

With this design, the beam emits from the first facet 716A along a first axis 795 and is directed along the first axis 795 at the beam reflector 725. Subsequently, the beam reflector 725 redirects a portion of the beam along a second axis 796 at the WD feedback assembly 726. In alternative, non-exclusive embodiments, the first axis 795 and the second axis 796 are at an axis angle 797 of approximately 30°, 45°, 60°, 75°, or 90° relative to each other. It should be noted that other axis angles 797 can be utilized.

In this embodiment, the WD feedback assembly 726 reflects a portion of the beam back to the gain medium 716 via the beam reflector 725, and the WD feedback assembly 726 is used to precisely select and adjust the lasing frequency of the external cavity 736 and the wavelength of the output beams 712. Thus, the WD feedback assembly 726 dictates what wavelength will experience the most gain and thus dominate the wavelength of the output beams 712. In FIG. 7, the WD feedback assembly 726 is similar to the WD feedback assembly 26 illustrated in FIGS. 4A and 4B and described above. Alternatively, the WD feedback assembly 726 can be similar to the corresponding WD feedback assemblies 526, 626 illustrated in FIGS. 5A-6B.

In this embodiment, the gain medium 716, the beam reflector 725, and the WD feedback assembly 726 cooperate to form the folded external cavity 736. Further, the folded configuration of the external cavity 736 can allow for a relatively longer external cavity 736 in an overall relatively small footprint. This allows for a smaller physical dimensioned laser source 710. In certain embodiments, for laser sources 710 employing rapid tuning, longer cavity lengths (e.g. approximately 10 centimeters) result in better pulse-to pulse stability and less frequency noise with tuning.

With the design illustrated in FIG. 7, the laser source 710 does not require an output optical assembly 24 (illustrated in FIGS. 1A and 1B). Stated in another fashion, because the gain medium 716 is emitting from only one facet 716A, only one optical assembly 718 is required. This can reduce the cost and complexity of the laser source 710.

Figure 8:
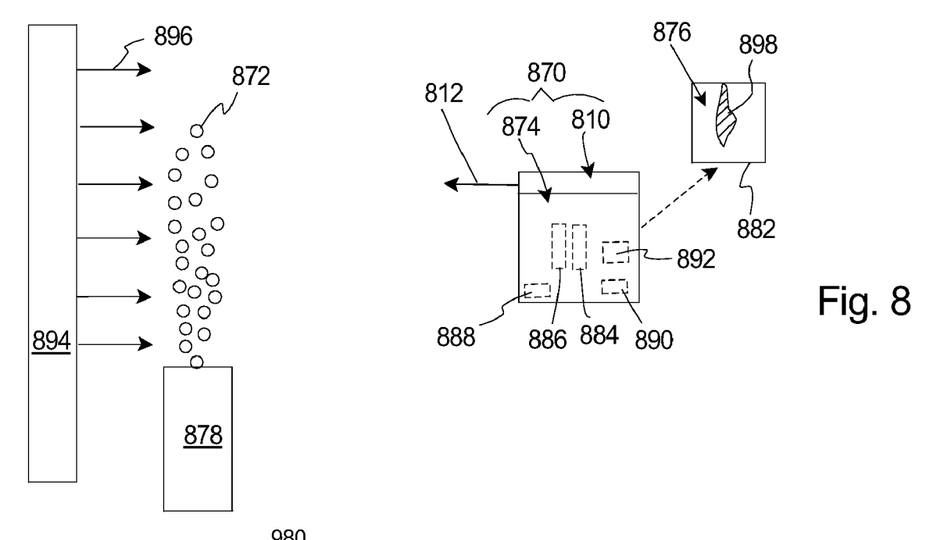
FIG. 8 is simplified illustration of a gas sensor system having features of the present invention and an emitting gas.

FIG. 8 is simplified illustration of a gas sensor system 870 having features of the present invention and an emitting gas 872. In this embodiment, the gas sensor system 870 includes (i) a laser source 810 that illuminates the area near the emitting gas 872, and (ii) an imager 874 (i.e. an infrared camera) that captures real-time, high resolution thermal images 876 of the emitting gas 872 that can be displayed or recorded for future viewing. As non-exclusive examples, the gas sensor system 870 is useful for locating emitting gas 872 (i.e. leaks) in the oil, gas, utility, chemical industries, as well as locating emitting gas 872 for homeland security.

In certain embodiments, because of the unique design disclosed herein, the gas sensor system 870 can be extremely compact, hand-held, lightweight, stable, rugged, small, self-contained, and portable. For example, the sensor system 870 can have dimensions of approximately 130 millimeters (height) by 145 millimeters (width) by 250 millimeters (length) (where length is taken along the propagation direction of the laser beam) or less.

In one embodiment, the type of emitting gas 872 detectable by the sensor system 870 can include any gas 872 having molecules that absorb ("absorption features") in the MIR range. A non-exclusive example of gases 872 having absorption features in the MIR range that can be detected includes, but is not limited to, (i) sulfur hexafluoride (SF6), (ii) Acetylchloride, (iii) Ethylene, (iv) Freon (such as dichlorodifluoromethane), (v) Propenal, (vii) Tricholorethylene, (viii) methane (CH4), (ix) ethylene (C2H4), (x) ethane (C2H6), (xi) hydrogen chloride (HCl), (xii) ammonia (NH3), (xiii) nitrous oxide (NO), (xiv) hydrazine (N2H4), and (xv) monomethyl hydrazine (MMH). Yet another example of gases 12 includes (i) chemical agents such as mustard gas or other gases that may pose problems for the military, and/or (ii) chlorine, hydrogen peroxide, or other gases that may pose problems for homeland security.

A non-exclusive list of possible gas sources 878 of the emitting gas 872 includes containers, power plants, industrial equipment, gas lines, storage tanks, and electrical equipment.

The laser source 810 can be similar in design to the laser sources 10 described above. For example, the laser source 710 can rapidly and accurately generate one or more sets of sequential, wavelength specific output beams 812 that span a predetermined detection range (e.g. the mid-infrared range).

The imager 874 captures the thermal image 876 of the emitting gas 872 and the surrounding environment. In one embodiment, the imager 874 is an infrared camera that provides real-time, high resolution thermal images 876 of the emitting gas 872 that can be displayed on a display 882 or recorded for future viewing. In FIG. 8, for convenience, the display 882 is illustrated as being positioned away from the imager 874. However, the display 882 can be a screen that is attached to the imager 874.

In one embodiment, the imager 874 includes an image sensor 884 (illustrated in phantom), a filter assembly 886 (illustrated in phantom), a storage system 888 (illustrated in phantom), and an imager control system 890.

The image sensor 884 receives the light that passes through the filter assembly 786 and converts the light into electricity. Examples of suitable image sensors 884 can include microbolometers, quantum well infrared photodetectors, or thermal light valve technology sold by Redshift Systems Corporation, located in Burlington, Mass.

The filter assembly 886 limits the wavelength of the light that is directed at the image sensor 884. For example, if the imager 874 is designed to detect any gas that absorbs in the MIR range, the filter assembly 886 can be designed to transmit all light in the MIR range, and block all light having a wavelength that is greater or lesser than the MIR range. With this design, the image sensor 884 responds primarily to desired wavelength, and ignores other background thermal emissions.

The storage system 7888 stores the various images. Non-exclusive examples of suitable storage systems 888 include flash memory, a floppy disk, a hard disk, or a writeable CD or DVD.

The imager control system 890 is electrically connected to and controls the operation of the electrical components of the imager 874. The imager control system 790 can include one or more processors and circuits and the imager control system 890 can be programmed to perform one or more of the functions described herein. The imager control system 890 receives information from the image sensor 884 and generates the image 876. Additionally, or alternatively, the imager control system 890 can further enhance the image 876 with color or other features that will further identify the location or type of emitting gas 872. In certain embodiments, the imager control system 890 can analyze the information from one or more images 876 to identify the one or more specific emitting gases 872 that are present and/or determine the quantity of one or more emitting gases 872 that are present.

In FIG. 8, the imager 874 and the laser source 810 share a common housing. Alternatively, the imager 874 and the laser source 810 can have separate housings.

Additionally, the imager 874 can include a battery 892 (illustrated in phantom) for powering the imager 874. This allows for the portable operation of the imager 874 in remote locations. Alternatively, for example, the imager 874 and the laser source 810 can share a common battery, or the sensor system 870 can be connected with an electrical cord to a power outlet.

As illustrated in FIG. 8, the output beams 812 are directed at a background 894 near a possible site of a gas leakage. The imager 874 captures both backscattered light 896 (illustrated as arrows) that is reflected off of the background 894 and background radiation. When a detectable emitting gas 872 is present, the backscattered light 896 is highly attenuated. This produces a region of contrast or shadow 898 on the image 876 that corresponds to and clearly illustrates the emitting gas 872. The background 894 can be any object that reflects the output beams 812.

In one embodiment, the wavelength of the output beams 812 is synchronized with the imager 874 so that imager control system 890 knows the wavelength of the output beam 812 at the time each image 876 is captured so that the gas 872 captured in the image 876 can be specifically identified. For example, if the gas 872 appears in a first image captured when the output beam 812 is at a first center wavelength and the gas 872 does not appear in a second image when the output beam 812 is at a second center wavelength, the type of gas 872 captured in the first image can be identified if the value of the first wavelength is known.

More specifically, if it is desired to locate emitting gases X, Y, and Z, the laser source 810 can be controlled to generate a set of sequential, specific, different center wavelength output beams 812 that span a portion or the entire the MIR range. In this embodiment, after generating the set of output beams 812, the imager control system 890 can analyze the images 876 captured by the imager 874 and compare the images 876 to a lookup table (not shown) that includes the absorption profiles of the gases in interest. With this information, the imager control system 890 can identify the gases 872 detected and/or how much of each of the gases is present. Further, with this design, the sensor system 870 scans for a relatively large number of gases 872 that have absorption in the scanning range.

Figure 9:
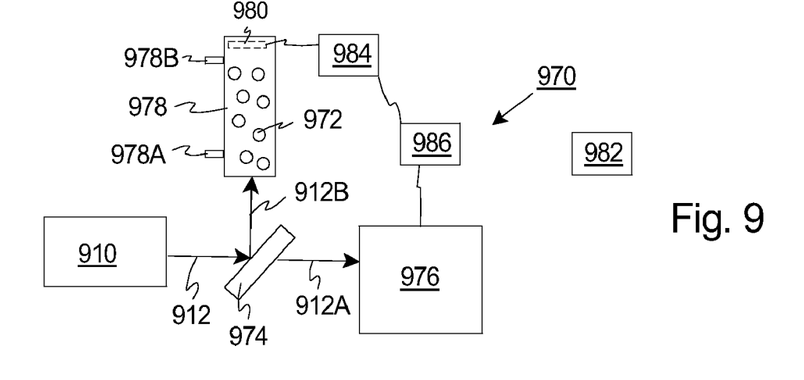
FIG. 9 is a simplified illustration of another embodiment of a gas sensor system having features of the present invention.

FIG. 9 is simplified illustration of another embodiment of a fluid sensor system having features of the present invention. In this embodiment, the fluid sensor system includes a laser source 910 (similar to those described above) that generates a plurality of output beams 912, and a spectrometer 970 that utilizes the output beams 912 to analyze one or more substance 972 (illustrated as circles). For example, the substance 972 can be a liquid, gas or solid.

In this embodiment, the spectrometer 970 includes (i) a beam splitter 974 that splits the output beams 912 into two beams 912A, 912B, (ii) a reference detector 976 that receives one of the beams 912A and that analyzes the beam 912A to determine the unattenuated power level, (iii) a sample area 978 (e.g. a container) that receives the other beam 912B and the one or more gases 972, (iv) a signal detector 980 (illustrated in phantom) that detects the beam 912B after travelling through the sample area 978, (v) control electronics 982 for powering the laser 910 and the spectrometer 970, (vi) acquisition electronics 984 for digitizing and integrating the detector signals from the signal detector 980, and (vii) analysis electronics 986 fro assembling the data into spectra and analyzing the spectra to determine the concentration and/or presence of different chemicals in the gases 972.

For example, the sample area 978 can be a container that receives the one or more substances 972. The sample area 978 can include an area input 978A and an area output 978B that allows the substances 972 to be changed in the sample area 978. In alternative embodiments, the sample area 978 receives a gas or condensed phase sample in a cell, or a condensed phase sample in an attenuated-total-reflectance (ATR) device.

While the particular systems as shown and disclosed herein is fully capable of obtaining the objects and providing the advantages herein before stated, it is to be understood that it is merely illustrative of the presently preferred embodiments of the invention and that no limitations are intended to the details of construction or design herein shown other than as described in the appended claims.

What is claimed is:

1. A laser source for emitting a set of output beams, with at least some of the output beams in the set having a different center wavelength, the laser source comprising:
  a gain medium having a first facet, the gain medium being adapted to generate a beam that exits the first facet;
  a feedback device positioned in the path of the beam, the feedback device redirecting at least a portion of the beam back to the gain medium;
  a device mover that adjusts an angle of incidence of the beam on the feedback device;
  a position detector that generates a position signal that relates to the angle of incidence of the beam on the feedback device; and
  a control system that selectively directs pulses of power to the gain medium based on the position signal from the position detector.

2. The laser source of claim 1 wherein the position detector includes a plurality of encoder marks and an optical reader that monitors the encoder marks; and wherein the control system selectively directs a pulse of power to the gain medium whenever the optical reader reads a predetermined number of encoder marks.

3. The laser source of claim 1 wherein the control system determines a center wavelength of the output beam based on the position signal.

4. The laser source of claim 1 wherein the feedback device includes a diffraction grating, and wherein the device mover rapidly adjusts the angle of incidence of the beam on the diffraction grating.

5. The laser source of claim 1 wherein the feedback device is moved to a plurality of alternative device positions with the device mover, and wherein the control system directs a pulse of power to the gain medium at each of the plurality of device positions so that the laser source generates the set of output beams.

6. A sensor system for imaging an emitting gas, the sensor system including the laser source of claim 1, and an imager that captures an image, and wherein the imager is synchronized with the pulses of power.

7. A sensor system for evaluating a gas, the sensor system including a container for receiving the gas, and the laser source of claim 1 directing the output beams into the container.

8. A laser source for emitting a set of output beams, with at least some of the output beams in the set having a different center wavelength, the laser source comprising:
  a gain medium having a first facet, the gain medium being adapted to generate a beam that exits the first facet;
  a feedback device positioned in the path of the beam, the feedback device redirecting at least a portion of the beam back to the gain medium;
  a device mover that adjusts an angle of incidence of the beam on the feedback device;
  a position detector that generates a position signal that relates to the angle of incidence of the beam on the feedback device; and
  a control system that selectively directs pulses of power to the gain medium, the control system determining a center wavelength of the output beam based on the position signal.

9. The laser source of claim 8 wherein the position detector includes a plurality of encoder marks and an optical reader that monitors the encoder marks; and wherein the control system selectively directs a pulse of power to the gain medium whenever the optical reader reads a predetermined number of encoder marks.

10. The laser source of claim 8 wherein the feedback device is moved to a plurality of alternative device positions with the device mover, and wherein the control system directs a pulse of power to the gain medium at each of the plurality of device positions so that the laser source generates the set of output beams.

11. A sensor system for imaging an emitting gas, the sensor system including the laser source of claim 8, and an imager that captures an image, and wherein the imager is synchronized with the pulses of power.

12. A sensor system for evaluating a gas, the sensor system including a container for receiving the gas, and the laser source of claim 8 directing the output beams into the container.

13. A laser source for emitting a set of output beams, with at least some of the output beams in the set having a different center wavelength, the laser source comprising:

a gain medium having a first facet, the gain medium being adapted to generate a beam that exits the first facet;
a feedback device positioned in the path of the beam, the feedback device redirecting at least a portion of the beam back to the gain medium;
a device mover that adjusts an angle of incidence of the beam on the feedback device;
a position detector that generates a first position signal when the feedback device is at a first device position and a second position signal when the feedback device is at a second device position; and
a control system that selectively directs pulses of power to the gain medium; the control system directing a pulse of power to the gain medium upon receipt of the first position signal, and directing another pulse of power to the gain medium upon receipt of the second position signal.

14. A sensor system for imaging an emitting gas, the sensor system including the laser source of claim 13, and an imager that captures an image, and wherein the imager is synchronized with the pulses of power.

15. A sensor system for evaluating a gas, the sensor system including a container for receiving the gas, and the laser source of claim 13 directing the output beams into the container.

16. A method for generating a set of output beams, with at least some of the output beams in the set having a different center wavelength, the method comprising the steps of:
generating a beam with a gain medium having a first facet that emits the beam;
positioning a feedback device in the path of the beam, the feedback device redirecting at least a portion of the beam back to the gain medium;
adjusting an angle of incidence of the beam on the feedback device with a device mover;
generating a position signal that relates to the angle of incidence of the beam on the feedback device; and
selectively directing pulses of power to the gain medium based on the position signal.

17. The method of claim 16 wherein the step of generating a position signal includes the steps of providing a plurality of encoder marks and monitoring the encoder marks with an optical reader; and wherein the step of selectively directing pulses of power includes directing pulses of power to the gain medium whenever the optical reader reads a predetermined number of encoder marks.

18. The method of claim 16 further comprising the step of determining a center wavelength of the output beam based on the position signal.

19. A method for generating a set of output beams, with at least some of the output beams in the set having a different center wavelength, the method comprising the steps of:
generating a beam with a gain medium having a first facet that emits the beam;
positioning a feedback device in the path of the beam, the feedback device redirecting at least a portion of the beam back to the gain medium;
adjusting an angle of incidence of the beam on the feedback device with a device mover;
generating a position signal that relates to the angle of incidence of the beam on the feedback device;
directing pulses of power to the gain medium; and
determining a center wavelength of the output beam based on the position signal.

20. The method of claim 19 wherein the step of adjusting includes moving the feedback device to a plurality of alternative device positions with the device mover, and wherein the step of directing pulses of power to the gain medium includes the step of directing a pulse of power to the gain medium at each of the plurality of device positions.

21. The method of claim 19 wherein the step of generating a position signal includes the steps of providing a plurality of encoder marks and monitoring the encoder marks with an optical reader; and wherein the step of directing pulses of power includes directing pulses of power to the gain medium whenever the optical reader reads a predetermined number of encoder marks.

22. A method for generating a set of output beams, with at least some of the output beams in the set having a different center wavelength, the method comprising the steps of:
generating a beam with a gain medium having a first facet that emits the beam;
positioning a feedback device in the path of the beam, the feedback device redirecting at least a portion of the beam back to the gain medium;
adjusting an angle of incidence of the beam on the feedback device with a device mover;
generating a first position signal when the feedback device is at a first device position;
generating a second position signal when the feedback device is at a second device position;
directing a pulse of power to the gain medium upon generation of the first position signal; and
directing a pulse of power to the gain medium upon generation of the second position signal.

* * * * *